United States Patent [19]

Hashizume et al.

[11] Patent Number: 4,560,793

[45] Date of Patent: Dec. 24, 1985

[54] PROCESS FOR PRODUCING TEREPHTHALIC ACID

[75] Inventors: Hiroshi Hashizume; Yoshiaki Izumisawa, both of Kitakyusyu, Japan

[73] Assignee: Mitsubishi Chemical Industries Limited, Tokyo, Japan

[21] Appl. No.: 306,762

[22] Filed: Sep. 29, 1981

Related U.S. Application Data

[63] Continuation of Ser. No. 860,479, Dec. 14, 1977, abandoned.

[30] Foreign Application Priority Data

Dec. 30, 1976 [JP] Japan ................................ 51-158987

[51] Int. Cl.$^4$ ............................................. C07C 51/16

[52] U.S. Cl. ..................................... 562/414; 562/416
[58] Field of Search ................................ 562/414, 416

[56] References Cited

U.S. PATENT DOCUMENTS 4,051,178 9/1977 Kimura et al. ...................... 562/416

Primary Examiner—Alan Siegel
Attorney, Agent, or Firm—Oblon, Fisher, Spivak, McClelland & Maier

[57] ABSTRACT

There is disclosed a process for the production of terephthalic acid by oxidizing para-xylene with molecular oxygen in which substantially all of the methyl acetate present in the vapor evolved from the reactor is recovered and circulated into the reactor.

9 Claims, 1 Drawing Figure

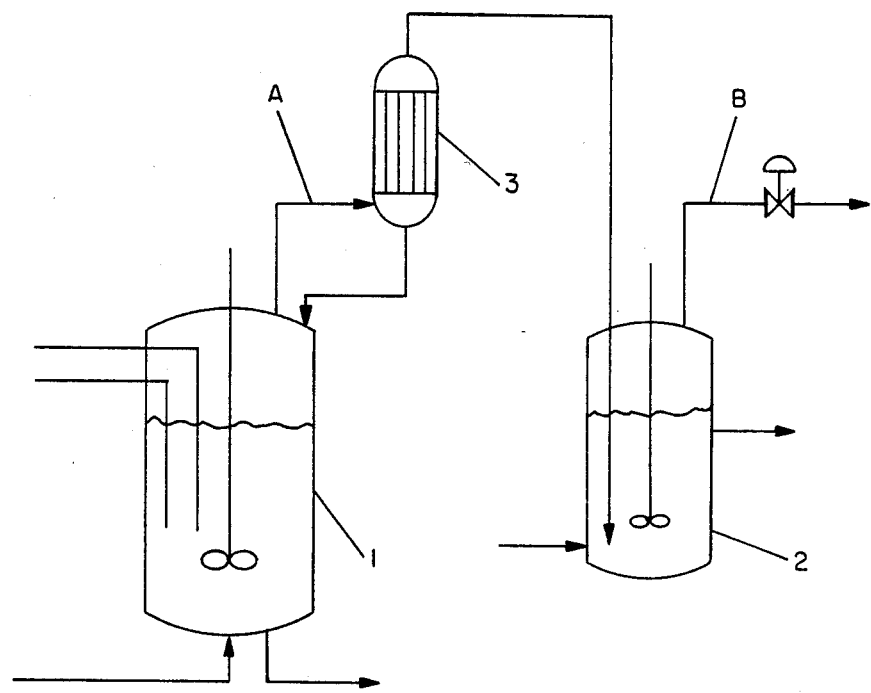
FIG. I

PROCESS FOR PRODUCING TEREPHTHALIC ACID

This is a continuation of application Ser. No. 860,479, filed Dec. 14, 1977 abandoned.

BACKGROUND OF THE INVENTION

1. Field of the Invention

This invention relates to a process for producing terephthalic acid by oxidizing para-xylene with molecular oxygen.

2. Description of the Prior Art

Oxidaton of para-xylene with molecular oxygen in acetic acid as solvent in the presence of a catalyst system containing bromine and one or more heavy metals such as cobalt, manganese and the like is well known as the S. D. method for the preparation of terephthalic acid. Although this method has various advantages for the commerical production of terephthalic acid, there remains a problem in that loss of acetic acid as the solvent takes place during the reaction and hence the S. D. method involves the defect of enhanced solvent loss. The principal causes for the acetic acid loss are considered to be the combustion of acetic acid and the formation of by-product methyl acetate. Among these, the combustion of acetic acid has already been investigated widely. It has been proposed that the combustion can be controlled by using, for example, specific reaction conditions or a specific catalyst system, and, to a certain degree, good results have been obtained thereby. However, the other principal cause for loss of the solvent, i.e., the formation of by-product methyl acetate has heretofore received little investigation.

SUMMARY OF THE INVENTION

Accordingly, it is an object of this invention to provide a process for supporting the formation of the by-product methyl acetate.

Briefly, this and other objects of this invention, as will hereinafter be made clear from the ensuing discussion, have been attained by recovering almost all of the methyl acetate present in the oxidation off-gas evolved from the reactor and circulating it into the reactor, thereby accomplishing this invention.

BRIEF DESCRIPTION OF THE DRAWING

FIG. 1 shows the experimental equipment used in the example of this invention wherein 1 denotes a reactor and 2, an absorption column.

DETAILED DESCRIPTION OF THE PREFERRED EMBODIMENTS

This invention is directed to a process for continuously producing terephthalic acid by oxidizing para-xylene with molecular oxygen in acetic acid as solvent in the presence of a catalyst system containing cobalt, manganese and bromine, characterized by recovering substantially all the methyl acetate present in the vapor evolved from the reactor and circulating it into the reactor.

This invention will be more specifically described hereinafter. The production of terephthalic acid contemplated herein includes any process in which para-xylene is oxidized with molecular oxygen in acetic acid solvent in the presence of a catalyst system containing cobalt, manganese and bromine for the production of terephthalic acid.

The reaction conditions employed in this invention include usually temperatures of 150° C. to 250° C., preferably 180° C. to to 220° C. and pressures of 1 to 50 kg/cm$^2$, preferably 10 to 30 kg/cm$^2$. The residence time in the reaction system may be, for example, on the order of 30 to 200 minutes.

Examples of the catalytic components usable in this invention include cobalt compounds such as cobalt acetate, cobalt naphthenate and the like; manganese compounds such as manganese acetate, manganese naphthenate and the like; and bromine compounds such as hydrogen bromide, sodium bromide, cobalt bromide, manganese bromide and the like. When cobalt bromide and/or manganese bromide is used, each of them can function as a source of two catalytic elements. Preferably hydrogen bromide is used as the bromine compound, since it makes the reaction more active, thereby making it possible to reduce the residence time and to control the combustion of the solvent. Usually the cobalt compounds are preferably used at a level of 100 to 500 ppm (as Co metal), the manganese compounds at a level of 50 to 1,000 ppm (as Mn metal) and the bromine compounds at a level of 500 to 3,000 ppm (as Br), each amount being based on the acetic acid solvent. Usually air is used for the molecular oxygen, which is provided in a proportion of 3 to 100 moles per mole of para-xylene. The acetic acid solvent is usually used, on a weight basis, in a proportion of 0.5 to 20 parts, preferably 1 to 10 parts per part of para-xylene.

It is an essential feature of this invention to recover substantially all the methyl acetate in the oxidation off-gas evolved from the reactor and to circulate it into the reactor. In prior art processes, only a very small portion of the methyl acetate in the oxidation off-gas would be condensed in a condenser together with acetic acid and circulated into the reactor, the remainder being delivered without condensing. From the off-gas thus delivered which is not condensed in the condenser, only acetic acid may be recovered by, for example, water scrubbing or similar means, but no methyl acetate is recovered by such means. In accordance with this invention, the methyl acetate present in the oxidation off-gas can be substantially entirely recovered and circulated into the reactor. Thus, this invention is based on our finding that an increased concentration of methyl acetate in the reaction mother liquor makes it possible to significantly hinder the side reaction from acetic acid to methyl acetate, thereby loss of acetic acid being greatly diminished. Substantially all, i.e., at least 80%, preferably at least 90% of the total methyl acetate present in the oxidation off-gas should be recovered for the purpose of this invention. If a smaller amount of methyl acetate is recovered and circulated, it is impossible to control sufficiently the formation of by-product methyl acetate. With the circulation of only a small portion of the methyl acetate as effected, for example, in the prior art processes, the concentration of methyl acetate in the reaction mother liquor will not reach the level required to suppress the undesirable side reaction, and therefore the results are far inferior to those obtained with this invention.

The recovery of methyl acetate contemplated herein may be effected by any procedure capable of recovering substantially all the methyl acetate from the oxidation off-gas. For example, the oxidation off-gas evolved from the reactor may be passed through a condenser to recover a portion of the methyl acetate in the vapor as the condensate and the condenser off-gas may be then subjected to absorption treatment with acetic acid to recover the remaining methyl acetate by means of absorption. Methyl acetate is hardly absorbed in water, but is readily absorbed in acetic acid. Thus the absorption of methyl acetate can be effected by contacting the condenser off-gas with acetic acid in, for example, a scrubber or an absorption column. In a preferred embodiment of this invention, a part of the acetic solvent to be supplied to the reactor is diverted to the absorption treatment and the resulting acetic acid solvent which contains methyl acetate absorbed therein is subsequently passed to the reactor. It is preferred to carry out the absorption procedure at as low a temperature as possible, usually below 50° C.

Alternatively, the methyl acetate in the oxidation off-gas may be recovered by condensing it in a condenser designed to possess such ability and construction as capable of cooling the oxidation off-gas adequately, under such conditions of temperature and gas flow rate that substantially all the methyl acetate can surely be condensed, and the condensate is circulated into the reactor.

In accordance with this invention, because of the substantially complete circulation of the methyl acetate in the oxidation off-gas into the reactor, the concentration of methyl acetate in the reaction mother liquor is always maintained at higher levels. Thus, in the reaction using hydrogen bromide as the bromine source for the catalyst system, the methyl acetate content will be on the order of 0.06 to 0.07% by weight in the prior art processes, whereas according to this invention it is at least 0.13% by weight, although the methyl acetate content of the reaction mother liquor may vary depending on the reaction conditions.

As stated above, in accordance with the invention, the formation of the by-product methyl acetate is significantly suppressed due to higher concentration of methyl acetate in the reaction mother liquor. As a result, the process according to this invention makes possible less acetic acid loss than the prior art processes and therefore it is quite economical and advantageous in commercial application. Having generally described this invention, a more complete understanding can be obtained by a comparative example and an example which are provided herein for purposes of illustration only and are not intended to be limiting in any manner.

EXAMPLE 1

The reaction of this example was carried out using the experimental equipment shown in FIG. 1.

Titanium pressure-resisting reactor (1) of 10 l capacity equipped with a reflux condenser (3), a stirrer, a heating device, a starting material inlet, a solvent inlet, an air inlet, a reaction slurry outlet and an off-gas outlet was charged with a solvent formulation having the following composition:

| Acetic acid | 2,990 g |
|---|---|
| Cobalt acetate | 4.44 g |
| (tetrahydrate) | (330 ppm as Co) |
| Manganese acetate | 4.68 g |
| (tetrahydrate) | (330 ppm as Mn) |
| Hydrobromic acid | 6.70 g |
| (aqueous 47% solution) | (1,000 ppm as Br) |
| Water | 154 g |
| | (5 wt. % water content) |

In the above all parts and percentage are based on the total weight of the formulation.

On the other hand, stainless steel pressure-resisting absorption column (2) of 10 l capacity equipped with an off-gas sparging inlet, an off-gas outlet, an acetic acid inlet and an acetic acid outlet was charged with 5 l of glacial acetic acid.

First reaction

A reaction was carried out in reactor (1) for 2 hours under such conditions that the temperature was 210° C., the pressure, 25 kg/cm² and the stirrer speed, 500 r.p.m. while para-xylene was supplied to reactor (1) at a rate of 500 g/hr. and simultaneously air was passed therethrough at such a rate that the oxygen content of the oxidation off-gas was kept at 4% by volume. Subsequently the reaction was continued for an additional 24 hours under the same conditions of temperature, pressure and stirring with para-xylene and air being supplied in the same way. During this period, a solvent formulation of the sme composition as above was additionally supplied at a rate of 1,5000 g/hr., while the reaction slurry was intermittently withdrawn from reactor (1) at intervals of 30 minutes to such a level that the volume of the slurry in the reactor was 4.5 l.

During the operation of reactor (1), the oxidation off-gas evolved therefrom was passed through absorption column (2), which was operated at a temperature of 30° C. and a pressure of 25 kg/cm² under stirring at a speed of 150 r.p.m. From two hours after the reaction had been stirred, glacial acetic acid was fed to the column at a rate of 500 g/hr. while the acetic acid in the column was intermittently withdrawn at intervals of 30 minutes to such a level that the volume of the acetic acid was 5 l. The acetic acid thus withdrawn was stored in a reservoir.

Second reaction

The acetic acid derived from the first reaction which contained methyl acetate absorbed therein was admixed with the catalyst components and fresh acetic acid so as to adjust the mixture to have the same composition as that of the above-mentioned solvent formulation except that 7.0 g of methyl acetate was also present for each 1,500 g amount of the formulation. Using the thus prepared solvent formulation, reactor (1) was operated for 12 hours under the same conditions as in the first reaction. The amount of methyl acetate formed in this reaction was determined and the results obtained are given in Table 1.

COMPARATIVE EXAMPLE

The amount of methyl acetate formed in the first reaction of Example 1 was determined. The results are also given in Table 1.

TABLE 1

|  | MeOAc in reaction mother liquor (g/hr.) | MeOAc in off-gas (A) from reactor (1) (g/hr.) | MeOAc in off-gas (B) from absorption column (2) (g/hr.) | MeOAc absorbed in acetic acid (g/hr.) | MeOAc supplied (g/hr.) | MeOAc formed* (g/hr.) |
|---|---|---|---|---|---|---|
| Example 1 (2nd reaction) | 2.4 (0.145% content) | 22.9 | 1.0 | 7.0 | 7.0 | 3.4 |
| Comp. Example (1st reaction) | 1.5 (0.09% content) | 14.3 | 0.6 | 4.4 | 0 | 6.5 |

MeOAc = methyl acetate
*The amount of methyl acetate formed was calculated by subtracting the amount of supplied methyl acetate from the total amount of methyl acetate removed out of the reactor, that is, the sum of the amount of methyl acetate in the reaction mother liquor plus that in off-gas (B) purged from the absorption column plus that absorbed in acetic acid.

Having now fully described the invention, it will be apparent to one of ordinary skill in the art that many changes and modifications can be made thereto without departing from the spirit or scope of the invention as set forth herein.

What is claimed as new and intended to be covered by letters patent is:

1. In a process for the continuous production of terephthalic acid by oxidizing p-xylene with molecular oxygen in acetic acid as a solvent in the presence of a catalyst system containing cobalt, manganese and bromine, the improvement comprising:
    recovering substantially all of the methylacetate present in the vapor evolved from the oxidation reactor; and
    recirculating said recovered methylacetate to the reactor.
2. The process of claim 1, wherein the reactor temperature is within the range of 180° C. to 220° C.
3. The process of claim 1, wherein the cobalt compound is present at the level of from 100 to 500 ppm (as Co metal), the manganese compound at the level of from 50 to 1,000 ppm (as Mn metal) and the bromine compound at the level of from 500 to 3,000 ppm (as Br), each component in the catalyst being based on the amount of acetic acid solvent.
4. The process of claim 1, wherein at least 80% of the methylacetate present in the vapor from said reactor is recovered.
5. The process of claim 1, wherein air is a source of molecular oxygen in said reaction and is present in an amount of 3 to 100 moles per mole of p-xylene.
6. The process of claim 1, wherein said acetic acid is present in said reaction in an amount of 0.5 to 20 parts by weight per one part by weight of p-xylene.
7. The process of claim 1, wherein said methylacetate in said vapor is substantially recovered in a single condenser.
8. The process of claim 1, wherein the catalyst is formed from a combination of cobalt bromide and manganese bromide.
9. The process of claim 1, wherein said oxidation reaction is conducted under a pressure to 1 to 50 kg/cm$^2$.

* * * * *